(12) United States Patent
Mensinger et al.

(10) Patent No.: US 12,191,017 B2
(45) Date of Patent: Jan. 7, 2025

(54) SYSTEMS AND METHODS FOR MEDICINE ADMINISTRATION AND TRACKING

(71) Applicant: Medtronic MiniMed, Inc., Northridge, CA (US)

(72) Inventors: Michael R. Mensinger, San Diego, CA (US); Angela R. Gaetano, San Diego, CA (US); Madison B. Smith, San Diego, CA (US); Heung Y. Im, La Jolla, CA (US); Francis W. Pascual, San Diego, CA (US); Jasper Benke, San Diego, CA (US); Sneha Thanasekaran, San Diego, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 684 days.

(21) Appl. No.: 17/209,083

(22) Filed: Mar. 22, 2021

(65) Prior Publication Data
US 2021/0295976 A1 Sep. 23, 2021

Related U.S. Application Data

(60) Provisional application No. 62/993,592, filed on Mar. 23, 2020.

(51) Int. Cl.
*G16H 20/17* (2018.01)
*A61M 5/20* (2006.01)
(Continued)

(52) U.S. Cl.
CPC .......... *G16H 20/17* (2018.01); *A61M 5/2033* (2013.01); *G16H 40/67* (2018.01); *G16H 50/30* (2018.01);
(Continued)

(58) Field of Classification Search
CPC ........ G16H 20/17; G16H 40/67; G16H 50/30; G16H 50/70; G16H 15/00; G16H 40/63;
(Continued)

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |

(Continued)

FOREIGN PATENT DOCUMENTS

WO 2019075352 A1 4/2019

OTHER PUBLICATIONS

D. El-Sappagh, S., Farman, A., Hendawi, A., Jun-Hyeog Jang, & Kwak, K. (2019). A mobile health monitoring-and-treatment system based on integration of the SSN sensor ontology and the HL7 FHIR standard. BMC Medical Informatics and Decision Making, 19, n/a. (Year: 2019).*

(Continued)

*Primary Examiner* — Amber A Misiaszek
(74) *Attorney, Agent, or Firm* — Carter, DeLuca & Farrell LLP

(57) ABSTRACT

A medicine administration and tracking system includes a delivery device configured to deliver a plurality of doses of medicine over a plurality of days and a computing device configured to receive dose information for each dose. The computing device includes a software application operable to cause the computing device to retrieve the dose information for all doses within a pre-determined period of days, categorize each dose within the pre-determined period of days into one of a plurality of time blocks throughout a 24-hour timeframe, determine a time of interest based on a time block of the plurality of time blocks having the least amount of doses categorized therein, and select a physiological parameter reading from a plurality of physiological (Continued)

parameter readings as a physiological parameter reading of interest based on a proximity of a time of the physiological parameter reading to the determined time of interest.

17 Claims, 5 Drawing Sheets

(51) Int. Cl.
*G16H 40/67* (2018.01)
*G16H 50/30* (2018.01)
*G16H 50/70* (2018.01)

(52) U.S. Cl.
CPC ....... *G16H 50/70* (2018.01); *A61M 2230/201* (2013.01)

(58) Field of Classification Search
CPC .......... A61M 5/2033; A61M 2230/201; A61M 2205/3561; A61M 2209/01; A61M 5/24; A61M 5/1723
USPC ......................................................... 705/2–3
See application file for complete search history.

(56) References Cited

U.S. PATENT DOCUMENTS

| | | | |
|---|---|---|---|
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,727,976 B2 * | 5/2014 | Iliff ........................ | G16H 50/20 600/300 |
| 9,672,328 B2 | 6/2017 | Saint et al. | |
| 2007/0123819 A1 | 5/2007 | Mernoe et al. | |
| 2008/0033749 A1 * | 2/2008 | Blomquist ............. | G16H 40/67 705/2 |
| 2008/0195416 A1 * | 8/2008 | Tribble .................. | G16H 50/70 700/231 |
| 2008/0249386 A1 * | 10/2008 | Besterman ............. | G16H 40/67 705/3 |
| 2010/0160861 A1 | 6/2010 | Causey, III et al. | |
| 2014/0156204 A1 * | 6/2014 | Taub ...................... | G16H 20/10 702/23 |
| 2015/0134356 A1 * | 5/2015 | Atlas .................. | A61B 5/14532 705/2 |
| 2017/0181645 A1 * | 6/2017 | Mahalingam .......... | G16H 10/60 |
| 2018/0000347 A1 * | 1/2018 | Perez ................. | A61N 1/36014 |
| 2018/0353698 A1 | 12/2018 | Saint et al. | |
| 2019/0252079 A1 | 8/2019 | Constantin et al. | |

OTHER PUBLICATIONS

International Search Report and Written Opinion issued in corresponding International Application No. PCT/US2021/023702 dated Jun. 28, 2021, 12 pages.

\* cited by examiner

SYSTEMS AND METHODS FOR MEDICINE ADMINISTRATION AND TRACKING

CROSS-REFERENCE TO RELATED APPLICATIONS

This application claims the benefit of U.S. Provisional Patent Application No. 62/993,592, filed on Mar. 23, 2020, the entire contents of which are hereby incorporated herein by reference.

FIELD

The present disclosure is related to medicine administration and tracking and, more specifically, to systems and methods for medicine administration and tracking utilizing contextualized data.

BACKGROUND

Diabetes mellitus ("diabetes") is a metabolic disease associated with high blood sugar due to insufficient production or use of insulin by the body. Diabetes affects hundreds of millions of people and is among the leading causes of death globally. Diabetes has been categorized into three types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. Gestational diabetes can occur during pregnancy when a pregnant woman develops a high blood glucose level. Gestational diabetes often resolves after pregnancy; however, in some cases, gestational diabetes develops into type 2 diabetes.

Various diseases and medical conditions, such as diabetes, require a user to self-administer doses of medicine. When administering a liquid medicine by injection, for example, the appropriate dose amount is set and then dispensed by the user, e.g., using a syringe, a medicine delivery pen, or a pump. Regardless of the particular device utilized for injecting the liquid medicine, it is important to track the medicine dosed, particularly for managing lifelong or chronic conditions like diabetes. To this end, some medicine administration systems include software applications that assist users with medicine administration and tracking, thereby helping users manage their diseases and/or medical conditions.

SUMMARY

Provided in accordance with aspects of the present disclosure is a medicine administration and tracking system including a medicine delivery device and a computing device. The medicine delivery device is configured to deliver a plurality of doses of medicine to a user over a plurality of days and to transmit, for each dose of the plurality of doses, dose information indicative of a time of delivery of the dose. The computing device is disposed in communication with the medicine delivery device and configured to receive the dose information for each dose of the plurality of doses. The computing device includes a data processing unit including a processor and a software application stored in a memory of the data processing unit and having instructions operable to cause the computing device to retrieve the dose information for all doses of the plurality of doses within a pre-determined period of days, categorize each dose of the plurality of doses within the pre-determined period of days into one of a plurality of time blocks throughout a 24-hour timeframe, determine, a time of interest based on a time block of the plurality of time blocks having the least amount of doses categorized therein, and select a physiological parameter reading from a plurality of physiological parameter readings as a physiological parameter reading of interest based on a proximity of a time of the physiological parameter reading to the determined time of interest.

In an aspect of the present disclosure, the system further includes a sensor device configured to obtain the plurality of physiological parameter readings and to transmit the plurality of physiological parameter readings to the computing device.

In another aspect of the present disclosure, the time of interest is a fasting period end time, the physiological parameter readings are blood glucose readings, and the physiological parameter reading of interest is a fasting blood glucose reading. In such aspects, the system may further include a blood glucose sensor device, e.g., a continuous glucose monitor, configured to obtain the blood glucose readings and to transmit the plurality of blood glucose readings to the computing device.

In another aspect of the present disclosure, the instructions are further operable to cause the computing device to determine a fasting period start time based on the fasting period end time, and select a blood glucose reading from the plurality of blood glucose readings as a pre-fasting blood glucose reading based on a proximity of a time of the blood glucose reading to the fasting period start time.

In still another aspect of the present disclosure, the fasting period start time is a sleeping start time, the fasting period end time is a sleeping end time, and a sleeping period is defined between the sleeping period start time and the sleeping period end time.

In yet another aspect of the present disclosure, the instructions are further operable to cause the computing device to determine whether a risk of hypoglycemia is too high and, where it is determined that the risk of hypoglycemia is too high, calculate a dose amount decrease for adjusting a dose amount delivered by the medicine delivery device.

In still yet another aspect of the present disclosure, determining whether a risk of hypoglycemia is too high is based upon the pre-fasting blood glucose reading and the fasting blood glucose reading.

A method of medicine administration and tracking provided in accordance with aspects of the present disclosure includes retrieving dose information for a plurality of doses of medicine delivered from a medicine delivery device to a user over a plurality of days, categorizing each dose of the plurality of doses into one of a plurality of time blocks throughout a 24-hour timeframe, determining a time of interest based on a time block of the plurality of time blocks having the least amount of doses of the plurality of doses, and selecting a physiological parameter reading from a plurality of physiological parameter readings as a physiological parameter reading of interest based on a proximity of a time of the physiological parameter reading to the determined time of interest.

In an aspect of the present disclosure, the time of interest is a fasting period end time, the physiological parameter readings are blood glucose readings, and the physiological parameter reading of interest is a fasting blood glucose reading.

In another aspect of the present disclosure, the method further includes determining a fasting period start time based on the fasting period end time, and selecting a blood glucose reading from the plurality of blood glucose readings as a pre-fasting blood glucose reading based on a proximity of a time of the blood glucose reading to the fasting period start time.

In yet another aspect of the present disclosure, the method further includes determining whether a risk of hypoglycemia is too high and, where it is determined that the risk of hypoglycemia is too high, calculating a dose amount decrease for adjusting a dose amount delivered by the medicine delivery device.

Another medicine administration and tracking system provided in accordance with the present disclosure includes a medicine delivery device and a computing device. The medicine delivery device is configured to deliver a plurality of doses of medicine to a user and to transmit, for each dose of the plurality of doses, dose information indicative of a time of delivery of the dose. The computing device is disposed in communication with the medicine delivery device and configured to receive the dose information for each dose of the plurality of doses. The computing device includes a data processing unit including a processor and a software application stored in a memory of the data processing unit and having instructions operable to cause the computing device to automatically tag or receive input instructions to tag a dose of the plurality of doses as a dose of interest associated with an event, identify a first physiological parameter reading from a plurality of physiological parameter readings as a pre-event physiological parameter reading, identify a second physiological parameter reading from the plurality of physiological parameter readings as a post-event physiological parameter reading, and determine whether a risk of an adverse physiological condition is too high based on the pre-event physiological parameter reading and the post-event physiological parameter reading.

In an aspect of the present disclosure, the system further includes a sensor device configured to obtain the plurality of physiological parameter readings and to transmit the plurality of physiological parameter readings to the computing device.

In another aspect of the present disclosure, the event is consumption of a meal, the physiological parameter readings are blood glucose readings, the pre-event physiological parameter reading is a pre-meal blood glucose reading, the post-event physiological parameter reading is a post-meal blood glucose reading, and the adverse physiological condition is hypoglycemia. In such aspects, the system may include a blood glucose sensor device configured to obtain the blood glucose readings and to transmit the blood glucose readings to the computing device.

In still another aspect of the present disclosure, determining whether the risk of hypoglycemia is too high is based upon the pre-meal blood glucose reading and the post-meal blood glucose reading.

Another method of medicine administration and tracking in accordance with the present disclosure includes retrieving dose information for a plurality of doses of medicine delivered from a medicine delivery device to a user over a plurality of days, automatically tag or receiving input instructions to tag a dose of the plurality of doses as a dose of interest associated with an event, identifying a first physiological parameter reading from a plurality of physiological parameter readings as a pre-event physiological parameter reading, identifying a second physiological parameter reading from the plurality of physiological parameter readings as a post-event physiological parameter reading, and determining whether a risk of an adverse physiological condition is too high based on the pre-event physiological parameter reading and the post-event physiological parameter reading.

In an aspect of the present disclosure, the event is consumption of a meal, the physiological parameter readings are blood glucose readings, the pre-event physiological parameter reading is a pre-meal blood glucose reading, the post-event physiological parameter reading is a post-meal blood glucose reading, and the adverse physiological condition is hypoglycemia.

The details of one or more aspects of the disclosure are set forth in the accompanying drawings and the description below. Other features, objects, and advantages of the present disclosure are apparent from the description and drawings, and from the claims.

DETAILED DESCRIPTION

Figure 1A:
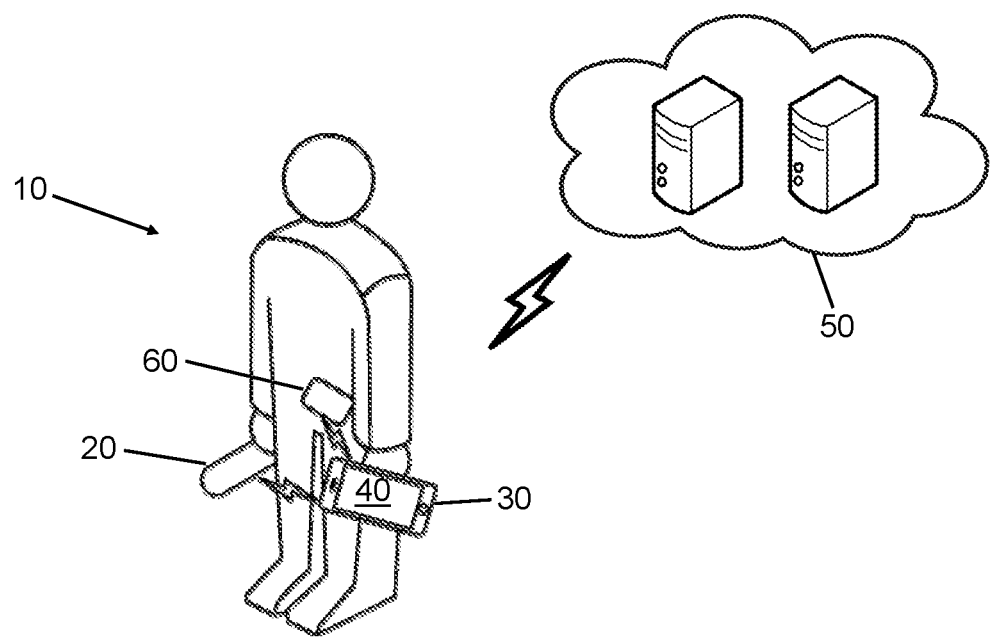
FIG. 1A is a schematic illustration of a medicine administration and tracking system provided in accordance with the present disclosure including a medicine delivery device, a computing device, and, in aspects, a sensor device and/or a data processing system.

FIG. 1A illustrates a medicine administration and tracking system 10 provided in accordance with the present disclosure. While the present disclosure is described herein for use for diabetes management involving an insulin pen, a health management application (e.g., a software application or app) associated with the insulin pen, and/or glucose monitoring devices, it is understood that the aspects and features of the present disclosure are also applicable to management of other diseases and medical conditions and/or for use with other medicine delivery devices and/or monitoring devices.

System 10 includes a medicine delivery device 20 in wireless communication with a computing device 30. Medicine delivery device 20 is detailed and illustrated herein as a medicine delivery pen, although any other suitable medicine delivery device may be provided such as, for example, a syringe, a pump, etc. Pen 20 is operable to select, set and/or dispense a dose of medicine. Computing device 30 is detailed and illustrated herein as a smartphone, although any other suitable computing device may be provided such as, for example, a tablet, a wearable computing device (e.g., a smart watch, smart glasses, etc.), a laptop and/or desktop computer, a smart television, a network-based server computer, etc. Pen 20 and/or smartphone 30 includes a health management application 40 associated with pen 20 and/or other devices part of or connected to system 10.

In aspects, system 10 further includes a data processing system 50 in communication with pen 20 and/or smartphone 30. Data processing system 50 can include one or more computing devices in a computer system and/or communication network accessible via the Internet (also referred to as "the cloud"), e.g., including servers and/or databases in the cloud.

Health management application 40 is paired with pen 20, which may be a prescription-only medical device, although other suitable devices are also contemplated. In aspects, the pairing of smartphone 30 with pen 20 at least partially unlocks health management application 40 to enable the user to utilize some or all features of the application 40 while providing secure access and ensuring pen 20 belongs to the user, e.g., who may have a prescription corresponding to use of some or all features of the health management application 40. Thus, the act of pairing unlocks and enables the functionality of health management application 40 and/or system 10; at least a portion of health management application 40 may be disabled without the specialized pairing and/or health management application 40 may provide only limited features without the specialized pairing.

Health management application 40, in aspects, can monitor and/or control functionalities of pen 20 and provide a dose calculator and/or decision support modules that can calculate and recommend a dose of medicine for the user to administer using pen 20.

Smartphone 30 can be used to obtain, process, and/or display contextual data that can be used to relate to the health condition of the user, including the condition for which pen 20 is used to treat. For example, smartphone 30 may be operable to track the location of the user; physical activity of the user including step count, movement distance and/or intensity, estimated calories burned, and/or activity duration; and/or interaction pattern of the user with smartphone 30. In aspects, health management application 40 can aggregate and process the contextual data to generate decision support outputs to guide and aid the user in using pen 20 and/or managing their behavior to promote treatment and better health outcomes.

In aspects, system 10 can include a sensor device 60 to monitor one or more health metrics and/or physiological parameters of the user. Examples of health metric and physiological parameter data monitored by sensor device 60 include analytes (e.g., glucose), heart rate, blood pressure, user movement, temperature, etc. Sensor device 60 may be a wearable sensor device such as a continuous glucose monitor (CGM) to obtain transcutaneous or blood glucose measurements that are processed to produce continuous glucose values. For example, the CGM can include a glucose processing module implemented on a stand-alone display device and/or implemented on smartphone 30, which processes, stores and displays the continuous glucose values for the user.

Figure 1B:
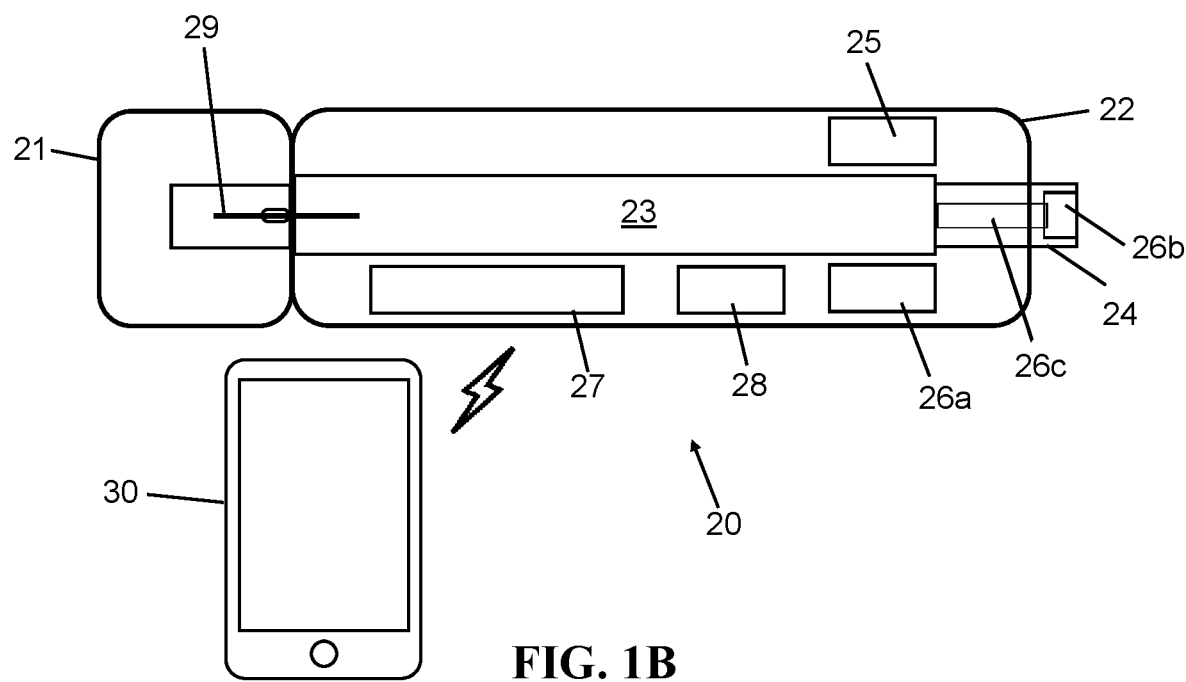
FIG. 1B is a block diagram of a medicine delivery pen in accordance with the present disclosure configured for use as the medicine delivery device of the system of FIG. 1A.

FIG. 1B shows pen 20 of system 10 although any suitable pen or, as noted above, any other suitable medicine delivery device may be utilized. Pen 20 includes a cap 21 configured to protect a medicine dispensing element (e.g., a needle 29) and a body 22 configured to contain a medicine cartridge 23 (e.g., which can be replaceable). Pen 20 further includes a dose dispensing mechanism 24 to dispense (e.g., deliver) medicine contained in medicine cartridge 23 out of pen 20 (e.g., through needle 29); a dose setting mechanism 25 to enable the selection and/or setting of a dose of medicine to be dispensed; an operations monitoring mechanism 28 (e.g., including one or more switches, sensors (electrical, optical, acoustic, magnetic, etc.), encoders, etc.) to qualitatively determine that pen 20 is being operated and/or to monitor the operation of pen 20 (e.g., to quantitatively determine an amount of medicine set and/or dosed); and an electronics unit 27 that can include a processor, a memory, a transceiver, and a battery or other suitable power source. Pen 20 is configured to pair to and communicate with health management application 40 operating on smartphone 30 (or, as noted above, other suitable computing device(s)).

In aspects, in order to operate pen 20, the user first sets e.g., dials, a dose using a dose knob 26a of dose setting mechanism 25. For example, the dose may be adjusted up or down to achieve a desired dose amount prior to administration of the dose by rotating dose knob 26a in an appropriate direction.

Once the appropriate dose has been set, the user applies a force against a dose dispensing button 26b of dose setting mechanism 25 to begin dispensing. More specifically, to begin dispensing, the user presses against the portion of dose dispensing button 26b that protrudes from body 22 of pen 20 to thereby drive a plunger 26c of dose dispensing mechanism 24 against an abutment (not explicitly shown) of medicine cartridge 23 to dispense an amount of medicine from cartridge 23 through needle 29 into the user in accordance with the dose amount set by dose setting mechanism 25, e.g., dose knob 26a, during setting.

In aspects, operations monitoring mechanism 28 of pen 20 senses movement of a rotating and/or translating component (e.g., plunger 26c, a drive shaft or screw (not shown) associated with plunger 26c, or other suitable component) of dose dispensing mechanism 24. Operations monitoring mechanism 28 may include one or more switches, sensors, and/or encoders for this purpose. More specifically, any suitable switch(es), sensor(s), and/or encoder(s) may be utilized to sense rotary and/or linear movement. Non-limiting examples of such include rotary and linear encoders, Hall effect and other magnetic-based sensors, linearly variable displacement transducers, etc. With respect to an encoder, for example, the encoder can be configured to sense the rotation of a drive screw that rotates to drive plunger 26c linearly; thus, by sensing rotation of the drive screw, the movement of the plunger 26c can be readily determined. Movement of the encoder may be detected as data processed by the processor of electronics unit 27 of pen 20, from which the amount of medicine dosed can be determined.

In aspects, the processor of electronics unit 27 of pen 20 can store the dose along with a timestamp for that dose and/or any other information associated with the dose. In aspects, the transceiver of electronics unit 27 enables pen 20 to transmit the dose and related information to smartphone 30. In such aspects, once the dose is transmitted, the dose data and any related information associated with that particular transmitted dose is marked in the memory of electronics unit 27 of pen 20 as transmitted. If the dose is not yet transmitted to smartphone 30 such as, for example, because no connection between the pen 20 and smartphone 30 is available, then the dose and associated data can be saved and transmitted the next time a successful communication link between pen 20 and smartphone 30 is established.

The timestamp may be the current time or a time from a count-up timer. When the dose and associated information is communicated to health management application 40 running on smartphone 30, the timestamp and/or "time-since-dose" parameter (as determined by the count-up timer) is transmitted by pen 20 and received by smartphone 30 for storage in memory 33 of data processing unit 31 of the smartphone 30 (see FIG. 1C). Where a count-up timer is utilized, the time of the dose can be determined without pen 20 having to know the current time, which can simplify operation and setup of pen 20. That is, health management application 40 can determined the time of dose based on the current time and the value returned from the count-up timer.

Dose dispensing mechanism 24 of pen 20 can include a manually powered mechanism, a motorized mechanism, or an assisted mechanism (e.g., a mechanism that operates partly on manual power and partly on motorized power). Regardless of the particular configuration of the dose dispensing mechanism 24, as noted above, when a force (e.g., a manual force, electrically-powered motor force, or combinations thereof) is applied to plunger 26c of dose dispensing mechanism 24, plunger 26c in turn provides a force to urge medicine from medicine cartridge 23 to deliver the set or dialed dose. In aspects, dose dispensing mechanism 24 can be adjusted to deliver the dose over a different period of time. In aspects, dose dispensing mechanism 24 can be operated such that plunger 26c is pushed by an adjustable tension spring or by a variable speed motor to inject the dose over a specific time frame (e.g., 1 s, 5 s, etc.) to help reduce the pain of dosing and/or for other purposes. In other aspects, dose dispensing mechanism 24 can be operated over a much longer period of time, e.g., to better match the dynamics of carbohydrates akin to an extended bolus delivered with a pump.

Health management application 40 of smartphone 30 provides a user interface to allow a user to manage health-related data. For example, health management application 40 can be configured to control some functionalities of pen 20 and/or to provide an interactive user interface to allow a user to manage settings of pen 20 and/or settings for smartphone 30 that can affect the functionality of system 10 (FIG. 1A).

Figure 1C:
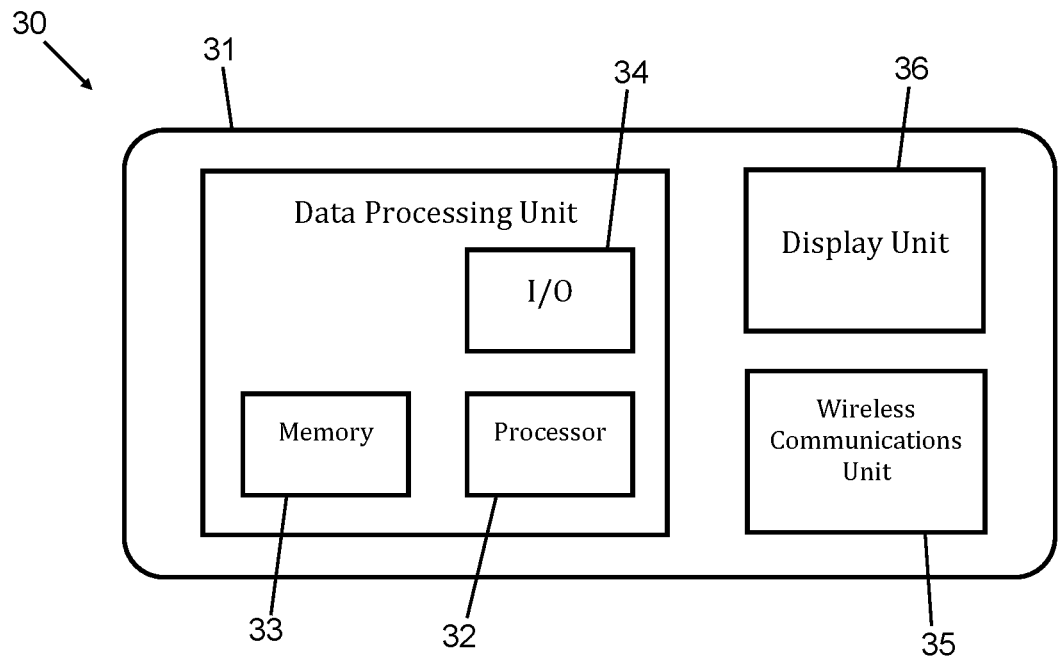
FIG. 1C is a block diagram of one configuration of the computing device of the system of FIG. 1A in accordance with the present disclosure.

FIG. 1C illustrates smartphone 30 of system 10 (FIG. 1A) including a data processing unit 31, a wireless communications unit 35, and a display unit 36. Data processing unit 31 includes a processor 32 to process data, a memory 33 in communication with the processor 32 to store data, and an input/output unit (I/O) 34 to interface processor 32 and/or memory 33 to other modules, units, and/or devices of smartphone 30 and/or external devices. Processor 32 can include a central processing unit (CPU) or a microcontroller unit (MCU). Memory 33 can include and store processor-executable code, which when executed by processor 32, configures the data processing unit 31 to perform various operations, e.g., such as receiving information, commands, and/or data, processing information and data, and transmitting or providing information/data to another device. In aspects, data processing unit 31 can transmit raw or processed data to data processing system 50 (FIG. 1A). To support various functions of data processing unit 31, memory 33 can store information and data, such as instructions, software, values, images, and other data processed or referenced by processor 32. For example, various types of Random Access Memory (RAM) devices, Read Only Memory (ROM) devices, Flash Memory devices, and other suitable storage media can be used to implement storage functions of memory 33. I/O 34 of data processing unit 31 can interface data processing unit 31 with wireless communications unit 35 to utilize various types of wired or wireless interfaces compatible with typical data communication standards, for example, which can be used in communications of data processing unit 31 with other devices such as pen 20, via a wireless transmitter/receiver (Tx/Rx), e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. I/O 34 of data processing unit 31 can also interface with other external interfaces, sources of data storage, and/or visual or audio display devices, etc. to retrieve and transfer data and information that can be processed by processor 32, stored in memory 33, and/or exhibited on an output unit of smartphone 30 and/or an external device. For example, display unit 36 of smartphone 30 can be configured to be in data communication with data processing unit 31, e.g., via I/O 34, to provide a visual display, an audio display, and/or other sensory display that produces the user interface of the health management application 40 (FIG. 1A). In some examples, display unit 36 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Figure 2:
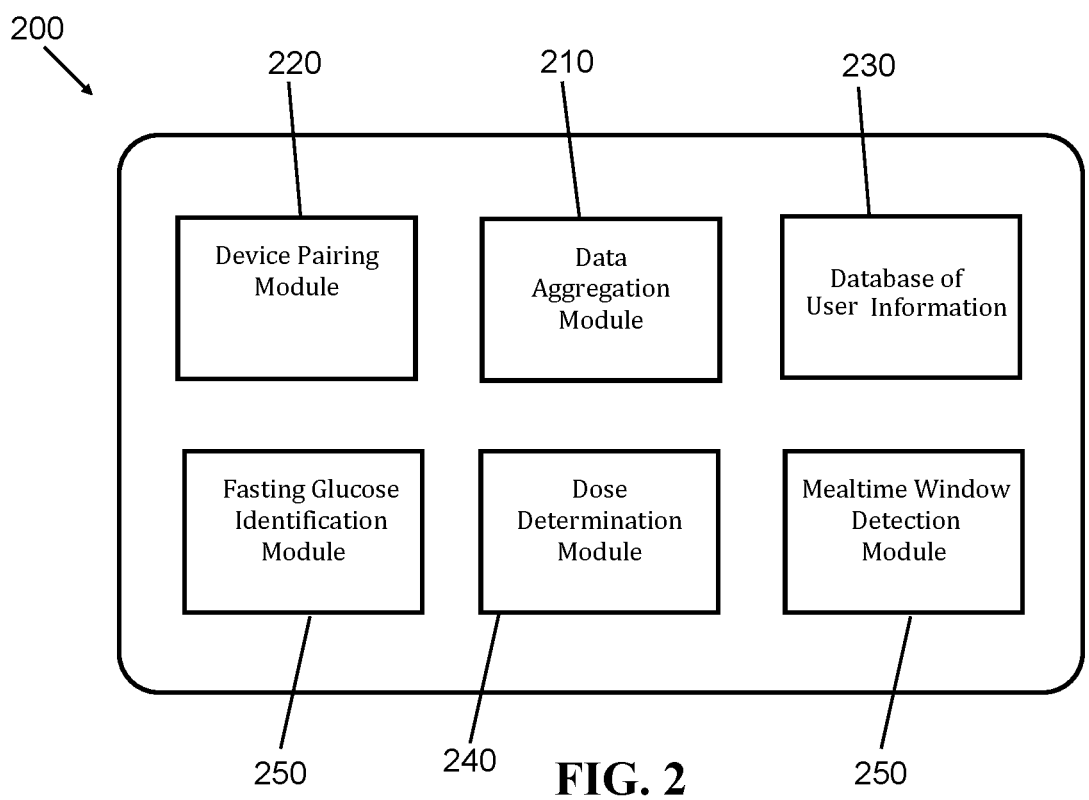
FIG. 2 is a block diagram illustrating a software architecture of various data processing modules configured for use with the system of FIG. 1A in accordance with the present disclosure.

Referring also to FIG. 2, once smartphone 30 receives the dose and related information (e.g., which can include time information, dose setting, and/or dose dispensing information, and other information about pen 20 and/or the environment as it relates to a dosing event), smartphone 30 stores the dose related information in memory 33, e.g., which can be included among a list of doses or dosing events. In aspects, via the user interface associated with health management application 40, smartphone 30 allows the user to browse a list of previous doses, to view an estimate of current medicine active in the patient's body ("medicine on board") based on calculations performed by health management application 40, and/or to utilize a dose determination module 240 to assist the patient regarding dose setting information on the size of the next dose to be delivered. For example, the patient may enter carbohydrates to be eaten and current blood sugar, and health management application 40 would already know insulin on board. Using these parameters, a suggested medicine dose (e.g., such as insulin dose), calculated by the dose determination module 240, may be determined. In aspects, smartphone 30 can also allow the user to manually enter dose data, e.g., boluses, which may be useful if the battery in pen 20 has been depleted or another medicine delivery device, e.g., a syringe, was utilized to dose.

Further features of system 10, including health management application 40 operable on smartphone 30, pen 20, and/or other suitable device(s) and configured to communicate with a medical device (e.g., pen 20 or other medicine delivery device) can be found in U.S. Pat. No. 9,672,328, entitled "Medicine Administering System Including Injection Pen and Companion Device," the entire contents of which are hereby incorporated herein by reference.

Continuing with reference to FIG. 2, in conjunction with FIGS. 1A-1C, a software architecture 200 of various data processing modules of health management application 40 of system 10 is shown generally including a data aggregation module 210, a device pairing module 220, a database of user information 230, a dose determination module 240, a fasting glucose identification module 250, and/or a mealtime window detection module 260. Some or all of the data processing modules 210-260 of software architecture 200 of health management application 40 may be provided on smartphone 30; additionally or alternatively, some or all of the data processing modules 210-260 may be provided on pen 20 (e.g., on electronics unit 27 thereof), data processing system 50 (in the cloud, e.g., resident on one or more cloud computers), and/or another device(s). Data processing modules 210-260 control functionalities of smartphone 30, pen 20, and/or another device(s) including aggregating and processing output signals transmitted by pen 20 to execute a device pairing for validation of the pen 20 and unlocking of some or all functionality of health management application 40, e.g., utilizing device pairing module 220, as noted above.

In aspects, some of the data processing modules 210-260 may be configured to process health metric data (e.g., CGM data, dose data, etc.) and contextual data obtained by health management application 40 from sensor device 60, other devices of system 10, other devices of the user, and/or other applications on smartphone 30. More specifically, data aggregation module 210 may be configured to obtain the health metric data from one or more devices, e.g., pen 20, sensor device 60, and/or other devices or applications in communication with health management application 40. Database 230 stores the health data and contextual data associated with the user and/or populations of users. In aspects, database 230 can be resident on data processing system 50, e.g., in the cloud.

Dose determination module 240, e.g., a dose calculator module, is configured to calculate a dose of medicine to be delivered from pen 20 based on time-relevant and context or circumstances-relevant data specific to the user of pen 20.

In aspects, software architecture 200 includes a fasting glucose identification module 250 configured to determine whether a glucose reading is a fasting glucose reading based in whole or in part upon time-relevant and context or circumstances-relevant dose data specific to the user of pen 20. Fasting glucose identification module 250 may further be configured to adjust or recommend adjustments to a basal dose based upon the identified fasting glucose reading(s). Fasting glucose identification module 250 is described in greater detail below.

In aspects, software architecture 200 includes a mealtime window detection module 260 configured to determine whether a dose delivered by pen 20 is a bolus dose associated with a meal. Mealtime window detection module 260 may further be configured, if the bolus dose is determined to be associated with a meal, to determine which meal of the day the delivered dose is associated with, assess the response to the bolus dose, and adjust or recommend adjustments to the bolus dose. Mealtime window detection module 260 is described in greater detail below.

The various data processing modules 210-260 of software architecture 200 can be organized to provide data to one another in various ways, including directly (e.g., module-to-module) and/or indirectly (e.g., via an intermediary module), based on a periodic, an intermittent, and/or a per-request basis. Additional or alternative data processing modules are also contemplated.

Referring generally to FIGS. 1A-2, fasting glucose is a glucose reading taken after a period of fasting (e.g., a willful abstaining of the intake of food for a period of time). Fasting glucose readings may be used in clinical decision processes as a primary data point for decisions related to increasing or decreasing basal or long acting insulin amounts (long acting insulin titration). In many instances, the fasting period occurs during an overnight period in which the user is asleep and the fasting glucose reading is obtained before the user has a first meal (or other food intake) of the day; however, this does not have to be the case, for example, in situations where a user may work at night and sleep during the day, or may otherwise have a prolonged fasting period during the day or night.

There are several different approaches to identifying fasting periods, sleep schedule, and/or fasting glucose readings. These approaches may be fully manual, part manual and part automatic, or fully automatic. For example, one manual approach requires a user to manually designate a blood glucose (BG) reading as fasting. This is the most direct approach, but since it is fully manual, relies on user consistency and may put additional burden on the user. Another approach requires a user to manually configure a reader device (e.g., health management application 40) with a typical overnight period specific to the user, allowing the health management application 40 to search for a BG reading at or near the end of the preconfigured overnight period and prior to the first rapid-acting or bolus dose of the day. This approach, although alleviating some burden, may be problematic, for example, if the user does not maintain a consistent sleep schedule. A system that automatically tags glucose readings as fasting removes the burden and/or problems associated with other methods and can increase the number of data points available for clinical decision support. Fasting glucose identification module 250 implements such a fully automated method, as detailed below.

Figure 3A:
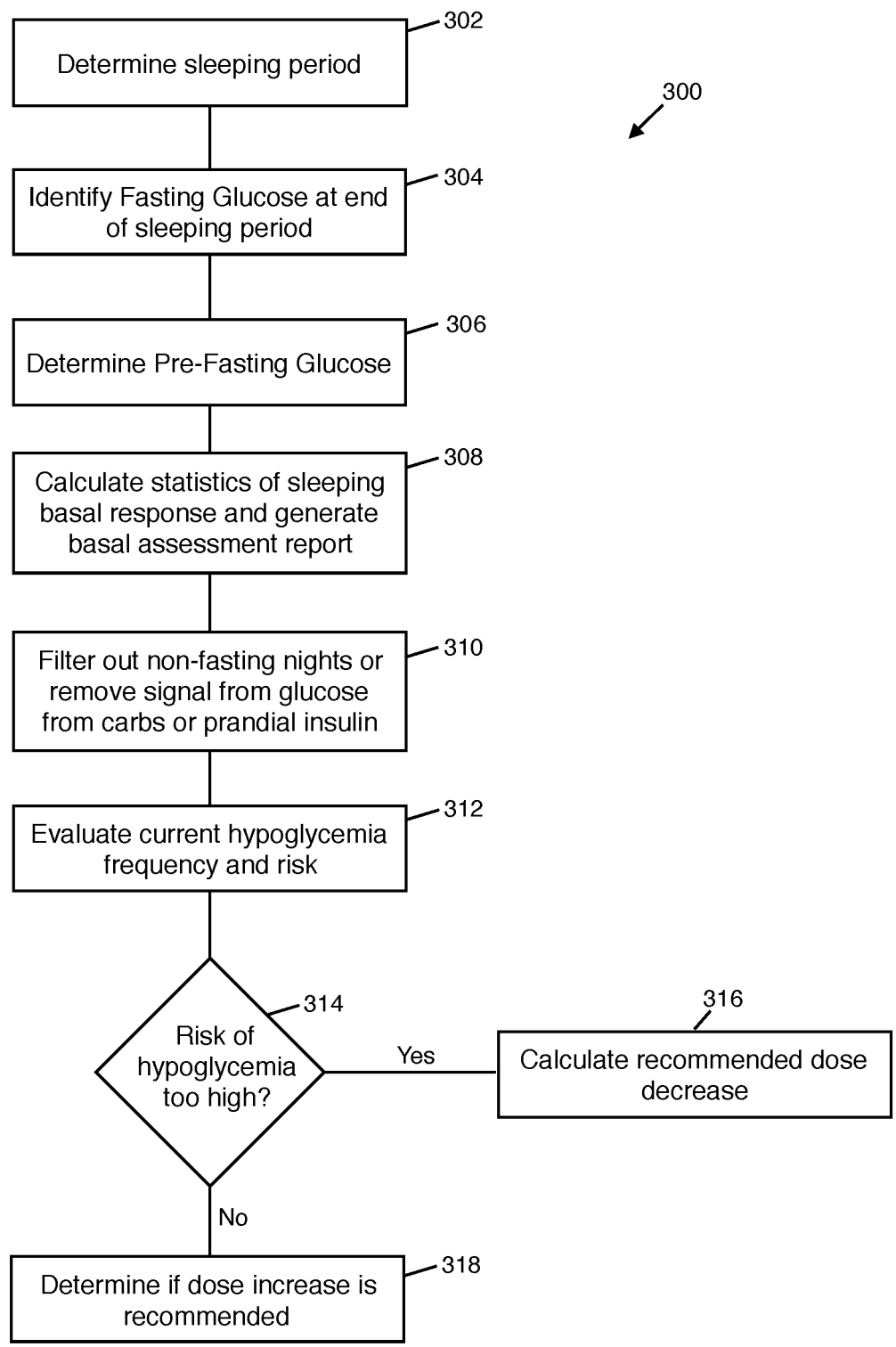
FIG. 3A is a flowchart illustrating a method of identifying a fasting glucose reading and determining a dose recommendation based thereon in accordance with the present disclosure.

Turning to FIG. 3A, a fully automated method in accordance with the present disclosure to be implemented by fasting glucose identification module 250 (or any other suitable module or groups of modules) is shown as method 300. Method 300 enables the identification of a fasting glucose reading and, based thereon, enables adjustments to or recommendations to adjust, if necessary, the user's basal dose. This is accomplished, as described in greater detail below, based on identifying a fasting (e.g., sleeping) period, determining a fasting glucose value and time, determining a pre-fasting glucose value and time, generating a report including a basal assessment graph, and using the generated report to adjust or recommend adjustments to the user's basal dose, if necessary.

Method 300 is initiated, for example, when a user selects to initiate a report on an interactive display of smartphone 30. Upon initialization of method 300, a sleeping period (or other fasting period) of the user is determined, as indicated at step 302. In aspects, the sleeping period may be defined as a single, static sleeping period based on recent history of user activity relative to sleeping times. In other aspects, the sleeping period may be dynamically defined on a daily basis using time-specific data related to actual user bedtime and wake time. In still other aspects, the sleeping period is determined using only thee user's dose data. In yet other aspects, the sleeping period is determined using only the user's blood glucose data (e.g., using CGM data to look for glucose spikes indicating eating, dawn phenomenon, etc.). In still yet other aspects, the sleeping period is determined using a combination of the user's dose and blood glucose data. In other aspects, the sleeping period is determined using the user's dose and/or blood glucose data, in addition to one or more of application interaction data, activity data from sensors on wearables (e.g., smart watch, smart health monitor, etc.), activity data from sensors on a smartphone or other connected device, a movement sensor, e.g., an accelerometer, to determine if the user is moving, and/or orientation sensor, e.g., a gyroscope, to determine if the user is laying down, standing, etc.

Figure 3B:
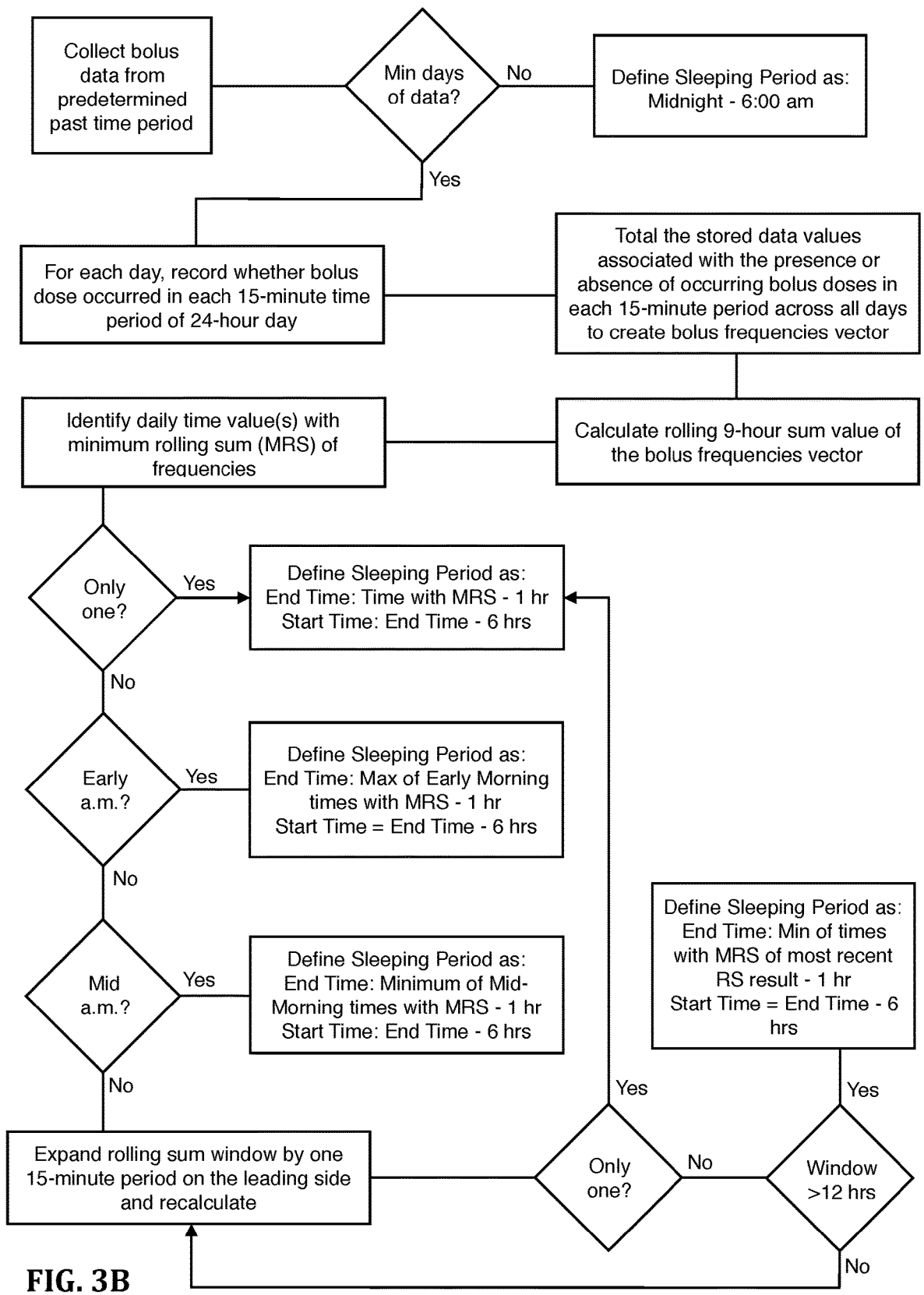
FIG. 3B is a flowchart illustrating a method of determining a sleeping period in accordance with the present disclosure.

FIG. 3B provides an exemplary sub-method of determining the sleeping period in step 302 of method 300. Referring to FIG. 3B, initially, the processing unit collects all bolus dose data from a predetermined past time period, for example the prior thirty (30) calendar days stored in the memory unit, and uses this information to define a "Sleeping Period" value. The bolus data, e.g., as dose data with timestamp information, may be communicated from pen 20 (FIG. 1A) to health management application 40 (FIG. 1A) and/or between other devices in any suitable manner. In aspects, a specified minimum number of days of bolus dose data may be required to enable analysis to proceed. For example, if there are less than the specified minimum number of days (e.g., three days) of bolus dose data stored in the memory unit, then the processing unit may define the sleeping period as 12:00 midnight to 6:00 am, and the sub-method, having determined the sleeping period, ends. On the other hand, if there are more than the specified minimum number of days of bolus dose data stored in the memory unit, then the processing unit defines the sleeping period value based upon an analysis. The analysis, as detailed below, may be a rolling sum of a calculated bolus frequencies vector associated with a specified time period, for example a rolling period, e.g., 9-hour, sum of a calculated bolus frequencies vector. Other suitable methods for determined the sleeping period value are also contemplated.

Generally, the determination includes obtaining the bolus data for each day, bucketing or categorizing the bolus data for all days into time blocks throughout a 24-hour timeframe, and determining based on the least populated buckets, start and end sleeping times and, thus, a sleeping period therebetween. The determination is described in greater detail below.

Continuing with reference to FIG. 3B, where it is determined that there are more than the specified minimum number of days of bolus dose data stored in the memory unit, the processing unit analyzes the stored dose data to determine for each day whether a bolus dose occurred in a predetermined period of time, such as, for example, in each 15-minute time period (or 30-minute or other suitable time period) of a 24-hour day, and assigns a data value to each predetermined time period in which at least one bolus dose occurred. Next, the processing unit totals the stored data values associated with the presence or absence of occurring bolus doses in each predetermined (e.g., 15-minute) time period across all the days of the analyzed period (e.g., between 3 and 30 days). This results in the generation of a vector of bolus frequencies by predetermined (e.g., 15-minute) period.

With the vector of bolus frequencies having be generated, the processing unit calculates a rolling 9-hour (for example) sum value of the bolus frequencies vector (e.g., using thirty-six 15-minute periods). For the first 8 hours and 45 minutes of the time vector (in the present example), the rolling sum calculation includes the preceding nighttime values, if any. For example, at 6:00 am the rolling sum calculation will include the sum of the 9:00 pm through 12:00 midnight (e.g., 21:00-24:00) frequency values of the previous day and the 12:01 am through 6:00 am frequency values of the next day.

The processing unit then identifies the daily time value(s) that have the minimum rolling sum of frequencies. If the processing unit determines only one daily time value that has the minimum rolling sum of frequencies value, the sleeping period is determined by the processing unit by first calculating the "Sleeping End Time" as the time with minimum rolling sum minus 1 hour, and then calculating the "Sleeping Start Time" as the sleeping end time minus 6 hours. If the processing unit identifies more than one daily time value that has the minimum rolling sum of frequencies value, then the processing unit determines whether any of the identified time values occurred during a defined early morning timeframe (e.g. 5:00 am to 9:00 am) or a defined mid-morning timeframe (e.g. 9:00 am to 1:00 pm). If any of the identified times occurred during the early morning timeframe, the sleeping period is determined by the processing unit by first calculating the sleeping end time as the time value with the maximum of early morning time values with minimum rolling sum minus 1 hour, and then calculating the sleeping start time as the sleeping end time minus 6 hours. If the processing unit determines that no identified times occurred during the early morning timeframe, and if any of the identified times occurred during the mid-morning timeframe, the sleeping period is determined by the processing unit by first calculating the sleeping end time as the time value with the minimum of mid-morning time values with minimum rolling sum minus 1 hour, and then calculating the sleeping start time as the sleeping end time minus 6 hours.

If the processing unit determines that no identified times occurred during the early morning timeframe or the mid-morning timeframe, then the processing unit expands the rolling sum window by one predetermined (e.g., 15-minute) period on the leading/front side and then recalculates as detailed above. The processing unit continues this process until either one minimum sum value remains or the window size exceeds 12 hours. If one minimum sum value remains, then the sleeping period is determined by the processing unit by first calculating the sleeping end time as the time value with the minimum rolling sum minus 1 hour, and then calculating the sleeping start time as the sleeping end time minus 6 hours. If the window size exceeds 12 hours and there is no minimum sum value, then the sleeping period is determined by the processing unit by first calculating the sleeping end time as the minimum of times with minimum rolling sum of the most recent rolling sum result minus 1 hour, and then calculating the sleeping start time as the sleeping end time minus 6 hours.

Although detailed above with respect to a sleeping period, the above may likewise be utilized to identify a fasting period. In aspects, different timeframes (e.g., to replace or in addition to the early-morning and mid-morning timeframes) suitable for a particular fasting period may be utilized. Further, any of the exemplary time periods, e.g., the sleeping period lasting 6 hours, may be varied depending upon settings and/or for other purposes.

Referring back to FIG. 3A, once the sleeping period (or fasting period) is determined at step 302, the method proceeds to step 304 where a fasting glucose reading at the end of the sleeping period (or fasting period) is identified. For CGM users, e.g., wherein the sensor device 60 (FIG. 1A) is a CGM, the CGM 60 may be configured to transmit to the processing unit of smartphone 30 all data pertaining to glucose readings during the determined fasting period, which would include the fasting glucose reading at the end of fasting. For BG users, e.g., wherein the sensor device 60 (FIG. 1A) is a blood glucose meter, the processing unit accesses data stored in the memory unit and removes from consideration any glucose reading data that is within two hours after a bolus dose data point.

The processing unit identifies the fasting glucose value and time for each day of the predetermined past time period (e.g., up to 30 days). Generally, the fasting glucose value is determined based upon a proximity of a glucose value to the sleeping end time value. More specifically, within each day's glucose reading data set, the processor analyzes glucose data within a specified amount of time before and after the determined sleeping end time (e.g., a 7-hour period comprising two hours before the determined sleeping end time to five hours after the sleeping end time) to identify the glucose value that occurs closest to the sleeping end time, excluding any glucose value that occurs within a specified time period (e.g., up to 2 hours) after a bolus dose. This glucose value is identified as the fasting glucose value, and the fasting glucose time is recorded as the time at which the fasting glucose value was recorded. If the processing unit is unable to identify a fasting glucose value within these parameters, then the processing unit will use the sleeping end time value to define the fasting glucose time as a placeholder for that particular day in the analysis.

Proceeding to step 306, a pre-fasting or bedtime glucose value and time is identified for each day of the predetermined time period (e.g., up to 30 days). To accomplish this, the processor analyzes each day's glucose data within a specified time period before the determined sleeping start time (e.g., a 7-hour period comprising twelve hours before the determined sleeping start time to five hours before the sleeping start time) to identify the glucose value (that is not prior to a bolus dose) that occurs closest to the sleeping start time. This glucose value is identified as the pre-fasting glucose value, and the pre-fasting glucose time is recorded as the time at which the pre-fasting glucose value was recorded.

Next, at step 308, statistics of the overnight basal response are calculated and, based thereon, a report is generated to enable the user, a physician, and/or health management application 40 (FIG. 1A) to act on to adjust or recommend adjustments to treatment, e.g., to a basal bolus dose. If the user is a continuous glucose monitor (CGM) user, then the basal assessment fasting window is the same as the sleeping period, which is recorded on a daily basis by the user's CGM device and may be transmitted to smartphone 30 for data storage and/or data processing. If the processing unit determines that there are zero days having both a pre-fasting glucose value and a fasting glucose value identified, and the requested report is a 30-day or 90-day report (for example), then the processing unit may include additional days (e.g., up to 30 days) until the processing unit identifies a day in which both the pre-fasting glucose and fasting glucose values were determined.

Following step 308, method 300 may proceed to step 310, in aspects, where the processing unit excludes from the generated report days in which the glucose data includes a bolus dose during the determined fasting/sleeping period. This exclusion addresses the challenge of disqualifying nights or subtracting modeled effects from fasting designation when the glucose response was modified by eating food or by administering medicine, e.g., prandial insulin injections, during the sleeping period or a predetermined time before the period, in order to get pure basal glucose response. If not utilized or required, method 300 proceeds to step 312.

In step 312 of method 300, the current hypoglycemia frequency and risk based on the generated fasting glucose values and basal assessment report is evaluated by a decision maker. The decision maker, e.g., user, physician, and/or health management application 40 (FIG. 1A) (via the processing unit), may then analyze the data and make a determination at step 314 as to whether the risk of hypoglycemia is too high. If the decision-maker determines that the risk of hypoglycemia is too high ("YES" at step 314), method 300 proceeds to step 316 where a recommended dose decrease is calculated. If the decision-maker determines that the risk of hypoglycemia is not too high ("NO" at step 314), method 300 proceeds to step 318 to determine whether a basal dose increase is recommended or if no change is recommended.

Figure 4:
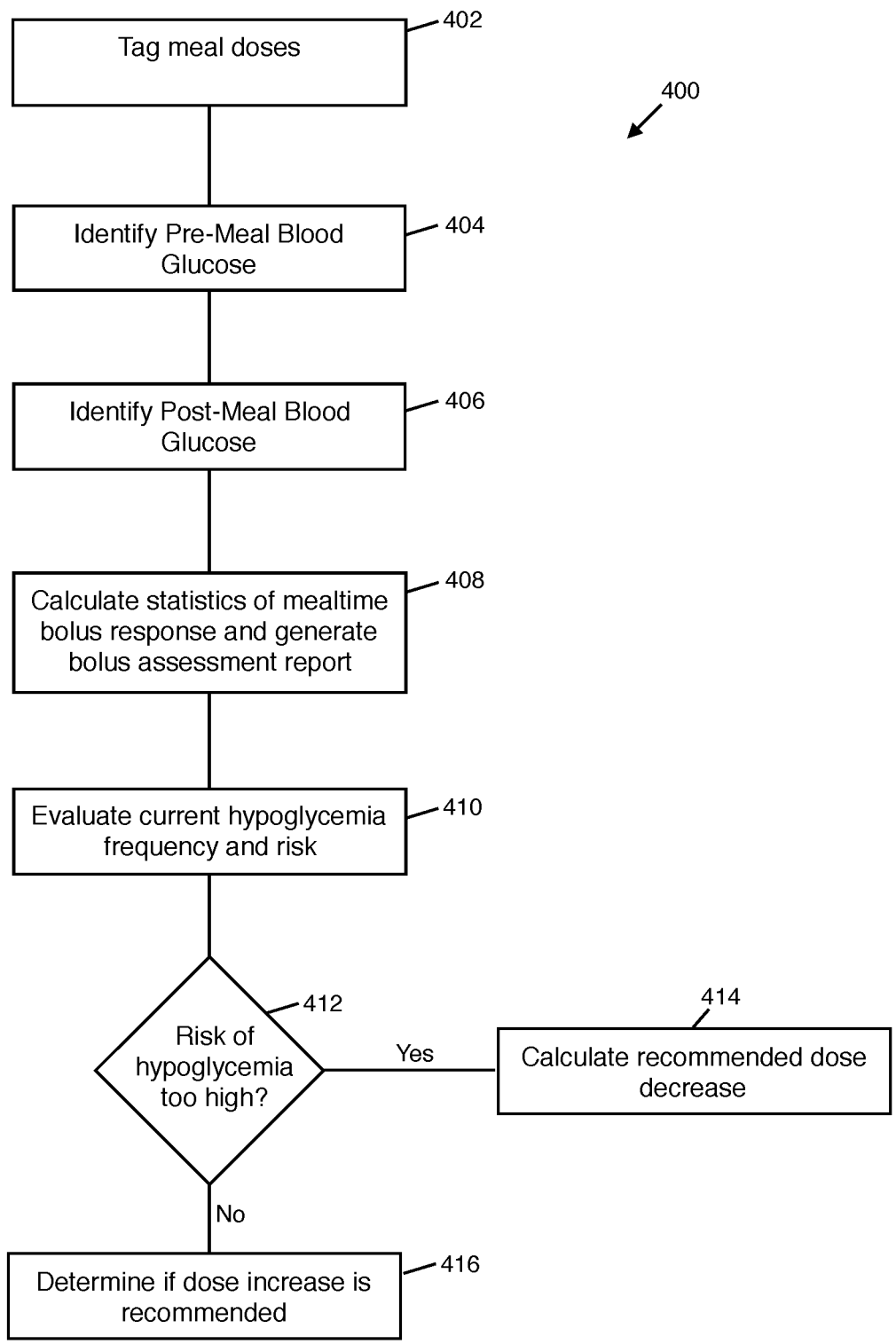
FIG. 4 is a flowchart illustrating a method of identifying a meal time window determining a dose recommendation based thereon in accordance with the present disclosure.

Turning to FIG. 4, also provided in accordance with the present disclosure is a fully automated method 400 to be implemented by mealtime window assessment module 260 (FIG. 2) for detecting a mealtime window and adjusting or recommending adjustment, if necessary, to a user's bolus dose associated with the detected mealtime window by identifying the mealtime window, tagging the mealtime bolus dose to the mealtime window, tagging pre-meal glucose readings, tagging post-meal glucose readings, generating a report including a bolus assessment, and using the generated report to adjust or recommend adjustments to the patient user's bolus dose associated with each meal window.

Method 400 begins at step 402 by tagging meal doses. This may be accomplished by the user tagging the meal dose manually, or by the processing unit executing a set of instructions in health management application 40 (FIG. 1A) to automatically tag meal dose. Automatic tagging of mealtime bolus doses may be accomplished by the processing unit collecting and tagging meal dose data from a predetermined past time period (e.g., the prior fourteen calendar days) stored in the memory unit. The processing unit then classifies the meal doses for a given meal according to specific criteria. For example, in a carbohydrate counting mode, the processing unit determines, as the meal dose, the dose with the largest amount taken in the meal window net of correction. More specifically, the processing unit compares the dose amount values that may be attributed to the size values for the associated meal (e.g., the total dose size minus the correction amount based on Insulin-on-Board (IOB) and glucose at the time of the meal), and determines the dose having the largest dose amount value to be the meal dose. For meal estimation and fixed dose modes, if a dose with a paired recommendation for that meal exists in the meal window, the processor determines that dose to be the meal dose. If multiple doses match these criteria in a given meal window, the processing unit determines the first such dose to be the meal dose.

If the processing unit identifies doses with paired recommendations that are tagged as a different meal than the evaluated meal window, the processing unit will exclude the glucose data of the evaluated meal window for the particular day. For example, a dose recommendation tagged for breakfast while in the time window of dinner will be excluded by the processing unit from the dinner window for that day. Where there are multiple dose recommendations in one meal window on a particular day, if one of the recommendations is for the correct meal window, the day is still included.

When no dose with a paired recommendation exists in a meal window, the processing unit will determine the meal dose as the dose with the largest dose amount value taken in the meal window net of correction. When no dose with a paired recommendation exists and the user is using a meal estimation function, the processing unit determines the size of the meal by matching the meal dose amount value net of correction to the nearest meal size setting. If the amount value is equidistant to two meal sizes, the processing unit classifies the dose as the smaller of the two meal sizes.

In aspects, the correction amount may be calculated and subtracted only if the insulin sensitivity factor (ISF), target blood glucose, and a blood glucose within a trailing predetermined period of time (e.g., the last 10 minutes) of the dose are available.

Once the meal doses have been tagged in step 402, method 400 proceeds to step 404 wherein the pre-meal glucose values within each day are identified. To accomplish this, the processing unit accesses data stored in the memory unit and identifies the glucose values and times for each meal within a predetermined past time period (e.g., the prior 14 days). Within each day's glucose data set, the processor analyzes glucose data within a specified (e.g., 1-hour) period before each meal dose to identify the glucose value that occurs closest to the meal time. This glucose value is identified as the pre-meal glucose value, and the pre-meal glucose time is recorded as the time at which the pre-meal glucose value was recorded.

Next, at step 406, the post-meal glucose values within each day are identified. To accomplish this, the processing unit accesses data stored in the memory unit and identifies the glucose values and times for each meal within the predetermined past time period (e.g., 14 days). Within each day's glucose data set, the processor analyzes glucose data (e.g., values and times) within a specified time period (e.g., 2 hours) after each meal dose to the earlier of 8 hours (for example) after the meal dose and the time of the next tagged meal dose. The processing unit determines the post-meal glucose value as the glucose value at the time that is closest to a predetermined time (e.g., 4 hours) after the meal dose.

Method 400 continued to step 408 wherein statistics of the mealtime bolus response are calculated and a report is generated for the user, physician, and/or health management application 40 (FIG. 1A) to act on to adjust or recommend adjustment to treatment. By way of example, the meal assessment window of the report may be a graph that is zero-aligned to the available pre-meal glucose times and wide enough to display the latest available post-glucose value. If the processing unit determines that there are zero days having both a pre-meal glucose value and a post-meal glucose value identified, and the requested report is a 30-day or 90-day report (for example), then the processing unit may include additional days (e.g., up to 30 days) until the processing unit identifies a day in which both the pre-meal glucose and post-meal glucose values were determined.

The next step 410 in method 400 is to evaluate the current hypoglycemia frequency and risk based on the generated meal window assessment report. The decision-maker, e.g., the user, physician, and/or the health management application 40 (FIG. 1A) (via the processing unit), may analyze the data and make a determination at step 412 as to whether the risk of hypoglycemia is too high. If the decision-maker determines that the risk of hypoglycemia is too high ("YES" at step 412), then method 400 proceeds to step 414 to calculate a recommended dose decrease for a particular meal window. If the decision-maker determines that the risk of hypoglycemia is not too high ("NO" at step 412), method 400 proceeds to step 416 where it is determined whether a bolus dose increase associated with a particular meal window is recommended or if no change is recommended.

The various aspects and features disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described functional and/or operational aspects may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing unit" as used herein may refer to any of the foregoing structure or any other physical structure suitable for implementation of the described techniques. Also, the techniques could be fully implemented in one or more circuits or logic elements.

While several aspects of the present disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. A medicine administration and tracking system, comprising:
  a medicine delivery device configured to deliver a plurality of doses of medicine to a user over a plurality of days, the medicine delivery device including:
    a sensor that measures a dose of the medicine dispensed from the medicine delivery device, wherein the medicine delivery device administers the dose of the medicine to the user to thereby cause the sensor to measure the dose of the medicine administered to the user by the medicine delivery device; and
    a processor configured to generate dose information associated with the dose of the medicine dispensed from the medicine delivery device as measured by the sensor and to wirelessly transmit, for each dose of the plurality of doses, dose information indicative of a time of delivery of the dose; and
  a computing device in communication with the medicine delivery device and configured to receive the dose information for each dose of the plurality of doses, the computing device including a data processing unit including a processor and a software application stored in a memory of the data processing unit and having instructions operable, when executed by the processor, to cause the computing device to:
    retrieve, from a signal wirelessly transmitted from the medicine delivery device to the computing device, the dose information for all doses of the plurality of doses within a pre-determined period of days;

categorize each dose of the plurality of doses within the pre-determined period of days into one of a plurality of time blocks throughout a 24-hour timeframe;

determine, based on a time block of the plurality of time blocks having the least amount of doses categorized therein, a fasting period end time of the user; and select a physiological parameter reading from a plurality of physiological parameter readings as a physiological parameter reading of interest based on a proximity of a time of the physiological parameter reading to the determined fasting period end time of the user, wherein the medicine delivery device is used to administer an adjusted dose of the medicine to the user.

2. The medicine administration and tracking system according to claim 1, further comprising: a sensor device configured to obtain the plurality of physiological parameter readings and to transmit the plurality of physiological parameter readings to the computing device.

3. The medicine administration and tracking system according to claim 1, wherein the physiological parameter readings are a plurality of blood glucose readings and the physiological parameter reading of interest is a fasting blood glucose reading.

4. The medicine administration and tracking system according to claim 3, further comprising:

a blood glucose sensor device configured to obtain the plurality of blood glucose readings and to transmit the plurality of blood glucose readings to the computing device.

5. The medicine administration and tracking system according to claim 4, wherein the blood glucose sensor device is a continuous glucose monitor.

6. The medicine administration and tracking system according to claim 3, wherein the instructions are further operable, when executed by the processor, to cause the computing device to:

determine a fasting period start time based on the fasting period end time; and select a blood glucose reading from the plurality of blood glucose readings as a pre-fasting blood glucose reading based on a proximity of a time of the blood glucose reading to the fasting period start time.

7. The medicine administration and tracking system according to claim 6, wherein the fasting period start time is a sleeping start time, the fasting period end time is a sleeping end time, and wherein a sleeping period is defined between the sleeping period start time and the sleeping period end time.

8. The medicine administration and tracking system according to claim 6, wherein the instructions are further operable, when executed by the processor, to cause the computing device to:

determine whether a risk of hypoglycemia is too high; and where it is determined that the risk of hypoglycemia is too high, calculate a dose amount decrease for adjusting a dose amount delivered by the medicine delivery device.

9. The medicine administration and tracking system according to claim 8, wherein determining whether a risk of hypoglycemia is too high is based upon the pre-fasting blood glucose reading and the fasting blood glucose reading.

10. A method of medicine administration and tracking, comprising:

delivering a plurality of doses of medicine from a medicine delivery device to a user over a plurality of days;

measuring, via a sensor disposed within the medicine delivery device, each of the plurality of doses of the medicine delivered to the user, wherein the medicine delivery device administers the dose of the medicine to the user to thereby cause the sensor to measure the dose of the medicine administered to the user by the medicine delivery device;

receiving, at a computing device in communication with the medicine delivery device, a signal wirelessly transmitted from the medicine delivery device to the computing device, the signal including the plurality of doses of medicine delivered from the medicine delivery device to the user over the plurality of days as measured by the sensor;

categorizing each dose of the plurality of doses into one of a plurality of time blocks throughout a 24-hour timeframe;

determining, based on a time block of the plurality of time blocks having the least amount of doses of the plurality of doses, a fasting period end time of the user; and selecting a physiological parameter reading from a plurality of physiological parameter readings as a physiological parameter reading of interest based on a proximity of a time of the physiological parameter reading to the determined fasting period end time of the user, wherein the medicine delivery device is used to administer an adjusted dose of the medicine to the user.

11. The method according to claim 10, wherein the physiological parameter readings are a plurality of blood glucose readings and the physiological parameter reading of interest is a fasting blood glucose reading.

12. The method according to claim 11, further comprising:

determining a fasting period start time based on the fasting period end time; and selecting a blood glucose reading from the plurality of blood glucose readings as a pre-fasting blood glucose reading based on a proximity of a time of the blood glucose reading to the fasting period start time.

13. The method according to claim 12, further comprising:

determining whether a risk of hypoglycemia is too high; and where it is determined that the risk of hypoglycemia is too high, calculating a dose amount decrease for adjusting a dose amount delivered by the medicine delivery device.

14. The medicine administration and tracking system according to claim 1, wherein the instructions are further operable, when executed by the processor, to cause the computing device to:

set a default fasting period of the user based on the computing device receiving the dose information for a number of days of the predetermined period of days that is less than a predetermined threshold number of days.

15. The medicine administration and tracking system according to claim 1, wherein the instructions are further operable, when executed by the processor, to cause the computing device to:

generate, for each time block of the plurality of time blocks, a vector of bolus frequencies based on the dose information received for that time block across all the days of the predetermined period of days;

calculate a rolling sum value for each vector of bolus frequencies; and identify at least one daily time value across all the days of the predetermined period of days that has a minimum rolling sum value.

16. The method according to claim 10, further comprising:
setting a default fasting period of the user based on the computing device receiving the dose information for a number of days of the predetermined period of days that is less than a predetermined threshold number of days.

17. The method according to claim 10, further comprising:
generating, for each time block of the plurality of time blocks, a vector of bolus frequencies based on the dose information received for that time block across all the days of the predetermined period of days;
calculating a rolling sum value for each vector of bolus frequencies; and
identifying at least one daily time value across all the days of the predetermined period of days that has a minimum rolling sum value.

* * * * *